United States Patent
Schulz et al.

(10) Patent No.: US 8,188,736 B2
(45) Date of Patent: May 29, 2012

(54) PET/MR SCANNERS FOR SIMULTANEOUS PET AND MR IMAGING

(75) Inventors: Volkmar Schulz, Stolberg (DE); Torsten Solf, Aachen (DE); Johan Overweg, Uelzen (DE); Andreas Thon, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 414 days.

(21) Appl. No.: 12/521,907

(22) PCT Filed: Jan. 8, 2008

(86) PCT No.: PCT/IB2008/050046
§ 371 (c)(1), (2), (4) Date: Jul. 1, 2009

(87) PCT Pub. No.: WO2008/084438
PCT Pub. Date: Jul. 17, 2008

(65) Prior Publication Data
US 2010/0102813 A1    Apr. 29, 2010

Related U.S. Application Data

(60) Provisional application No. 60/884,486, filed on Jan. 11, 2007.

(51) Int. Cl.
*G01V 3/00* (2006.01)
(52) U.S. Cl. ....................................... 324/309
(58) Field of Classification Search .......... 324/300–322
See application file for complete search history.

(56) References Cited

U.S. PATENT DOCUMENTS

| | | | | |
|---|---|---|---|---|
| 4,939,464 A * | 7/1990 | Hammer | .................. | 324/318 |
| 4,942,302 A | 7/1990 | Koechner | | |
| 5,581,151 A | 12/1996 | Wheeler et al. | | |
| 6,492,657 B1 | 12/2002 | Burlefinger et al. | | |
| 6,946,849 B1 | 9/2005 | Lu | | |
| 7,323,874 B2 | 1/2008 | Krieg et al. | | |
| 7,626,389 B2 * | 12/2009 | Fiedler et al. | .................. | 324/309 |
| 7,626,392 B2 * | 12/2009 | Nistler et al. | .................. | 324/318 |
| 7,667,457 B2 * | 2/2010 | Linz et al. | ...................... | 324/307 |
| 7,847,552 B2 * | 12/2010 | Haworth et al. | .............. | 324/318 |
| 7,945,079 B2 * | 5/2011 | Rosen | .......................... | 382/128 |
| 8,064,981 B2 * | 11/2011 | Eberler et al. | ................ | 600/407 |
| 2001/0040219 A1 | 11/2001 | Cherry et al. | | |
| 2003/0090267 A1 | 5/2003 | Rubashov | | |

(Continued)

FOREIGN PATENT DOCUMENTS
DE    102005015071 A1    1/2008
(Continued)

*Primary Examiner* — Dixomara Vargas (57) ABSTRACT

In a combined system, a magnetic resonance (MR) scanner includes a magnet (10, 110) configured to generate a static magnetic field (B0) at least in a MR examination region (12) from which MR data are acquired. Radiation detectors (40, 41, 140) are configured to detect gamma rays generated by positron-electron annihilation events in a positron emission tomography (PET) examination region (70). The radiation 5 detectors include electron multiplier elements (60, 160) having a direction of electron acceleration (ae) arranged substantially parallel or anti-parallel with the static magnetic field (B0). In some embodiments, the magnet is an open magnet having first and second spaced apart magnet pole pieces (14, 15) disposed on opposite sides of a magnetic 10 resonance examination region, and the radiation detectors include first and second arrays (40, 41) of radiation detectors disposed with the first and second spaced apart magnet pole pieces.

17 Claims, 10 Drawing Sheets

U.S. PATENT DOCUMENTS

| | | |
|---|---|---|
| 2004/0004188 A1 | 1/2004 | Tai |
| 2006/0052685 A1 | 3/2006 | Cho et al. |
| 2006/0251312 A1 | 11/2006 | Krieg et al. |
| 2007/0007844 A1* | 1/2007 | Barbat .......................... 310/208 |
| 2010/0130848 A1* | 5/2010 | Lin et al. ...................... 600/410 |
| 2010/0220909 A1* | 9/2010 | Thielemans et al. .......... 382/131 |
| 2010/0251691 A1* | 10/2010 | Mills ............................... 60/202 |
| 2010/0289409 A1* | 11/2010 | Rosenthal ................. 315/111.81 |
| 2010/0290575 A1* | 11/2010 | Rosenthal ..................... 376/112 |
| 2011/0115485 A1* | 5/2011 | Subbarao ...................... 324/309 |

FOREIGN PATENT DOCUMENTS

| | | |
|---|---|---|
| WO | 03003038 A1 | 1/2003 |
| WO | 2004111681 A1 | 12/2004 |
| WO | 2006071922 A2 | 7/2006 |
| WO | 2006111869 A2 | 10/2006 |
| WO | 2006111883 A2 | 10/2006 |
| WO | 2006119085 A2 | 11/2006 |

* cited by examiner

PET/MR SCANNERS FOR SIMULTANEOUS PET AND MR IMAGING

CROSS REFERENCE TO RELATED APPLICATIONS

This application claims the benefit of U.S. provisional application serial no. 60/884,486 filed Jan. 11, 2007, which is incorporated herein by reference.

The following relates to the imaging, diagnostic, and related arts. It finds particular application in simultaneous magnetic resonance (MR) imaging and positron emission tomography (PET) imaging, and is described with particular reference thereto. However, the following finds more general application in acquisition of PET and MR data from a common subject performed simultaneously, sequentially, in a time-interleaved fashion, or by some combination thereof, and to diagnostic processes using same such as imaging, magnetic resonance spectroscopy, and so forth.

MR and PET imaging are imaging modalities that can sometimes provide more information operating in concert than is provided by either modality operating alone. To maximize the synergy of combined MR and PET imaging, it would be useful to perform simultaneous MR and PET imaging, or at least to perform MR and PET imaging together over a relatively short time interval, for example while the subject remains stationary on a common patient bed with respect to the short time interval. Such integrated data acquisition would simplify spatial and optional temporal registration of images acquired by MR and PET, and would reduce the likelihood of occurrence of an operatively significant change in the patient or other subject between the MR and PET imaging data acquisitions. Other advantages of combined PET/MR imaging include the ability to use MR to construct an attenuation map for use in PET imaging, and the use of MR and PET together for motion compensation.

However, construction of a combined PET/MR scanner (sometimes called a hybrid PET/MR scanner) has heretofore been hindered by detrimental effect of the magnetic field of the MR acquisition sub-system on the photomultiplier tube (PMT) detectors of the PET acquisition sub-system. PMT detectors operate by avalanche multiplication of electrons. In a typical PMT arrangement, a photocathode is biased negatively. A photon striking the photocathode generates an initial burst of one or more electrons that travel through vacuum to a first dynode, where they induce generation of a larger number of electrons that travel through vacuum to a second dynode, and so forth, until the avalanche-multiplied electron burst reaches the anode. For PET applications, the PMT detector is typically arranged to view a scintillator that generates a burst of light (i.e., ultraviolet, visible, and/or infrared photons) responsive to interaction with a 511 keV gamma photon generated by a positron-electron annihilation event.

As the PMT operation is based on travel of electrons (which are charged particles) through a vacuum, a force proportional to the cross-product of the electron charge times the electron velocity and the magnetic field is exerted. This force can be represented, for example, in a form such as $F=qv \times B$ where q is the electron charge, v is the electron velocity vector, B is the magnetic field vector, and F is the force exerted on the electron traveling at velocity v by the magnetic field B. The effect of magnetic field on the PMT operation is suitably explained as follows. The process of electron multiplication is done via an electrostatic field E in the PMT. If there is also a static magnetic field B present, the force on the electron is given by $F=q(E+v \times B)$ and so the electron no longer accelerates along the direction of the accelerating electric field E for $|v|>0$. In consequence the acceleration of the electron and thus the multiplication is disturbed by the presence of the magnetic field B. For example, if the velocity of the electron is calculated as a function of time assuming a magnetic field orthogonal to the accelerating electric field, the velocity of the electron is seen to be zero at specific points in time, which corresponds to a restart of the acceleration. The extreme sensitivity of typical PMT detectors is such that even the earth's magnetic field (typically about $3 \times 10^{-5}$ T to $6 \times 10^{-5}$ T) is sufficient to degrade PMT operation. The small magnetic field of the earth can be compensated by suitable calibration of the PMT detector. In contrast, a typical MR scanner generates a static ($B_0$) magnetic field of 0.2 T to 7 T, depending upon the strength of the main magnet, with higher-field MR scanners in development. The effect of this much larger $B_0$ magnetic field on the PMT operation cannot be adequately compensated by calibration.

One approach for overcoming this problem is to use a solid state radiation detector that is less sensitive to the magnetic field compared with a PMT-based detector. For example, International Publication WO 2006/111869 discloses PET/MR scanners that employ solid state silicon photomultipliers (SiPM) or avalanche photodiodes (APD) as radiation detectors. This solution involves use of SiPM, APD, or other non-conventional detectors.

Another approach for overcoming the PMT/MR magnetic field interaction is to move the PMT detectors out of the MR acquisition system, and hence away from the strong magnetic field. The scintillators remain in or near the MR acquisition system, and are coupled with the remote PMT detectors using fiber optical connections. This approach retains the conventional PMT-based detectors, but has the disadvantages of increased system complexity. An additional disadvantage for time-of-flight (TOF) PET imaging is that the fiber optical connections add significant light loss and transit time spread that adversely affect TOF calculations. Wavelength-dependent dispersion further complicates these TOF calculations and limits the temporal resolution achievable using fiber optical connections.

The following provides new and improved apparatuses and methods which overcome the above-referenced problems and others.

In accordance with one aspect, a combined magnetic resonance (MR) and positron emission tomography (PET) data acquisition system is disclosed. A magnetic resonance scanner includes a magnet configured to generate a static magnetic field at least in a magnetic resonance examination region. The magnetic resonance scanner is configured to acquire magnetic resonance data from the magnetic resonance examination region. Radiation detectors are configured to detect gamma rays generated by positron-electron annihilation events in a positron emission tomography examination region. The radiation detectors include electron multiplier elements having a direction of electron acceleration arranged substantially parallel or anti-parallel with the static magnetic field.

In accordance with another aspect, a data acquisition method is disclosed. Magnetic resonance data are acquired using the magnetic resonance scanner of the combined MR and PET data acquisition system of the preceding paragraph. PET data are acquired using the radiation detectors of the combined MR and PET data acquisition system of the preceding paragraph. The MR and PET acquiring operations are performed simultaneously.

In accordance with another aspect, a combined magnetic resonance (MR) and positron emission tomography (PET) data acquisition system is disclosed. An open magnetic resonance scanner has first and second spaced apart magnet pole pieces disposed on opposite sides of a magnetic resonance examination region and is configured to generate a static magnetic field at least in the magnetic resonance examination region having a magnetic field direction directed from the first magnet pole piece to the second magnet pole piece. First and second arrays of radiation detectors are disposed with the first and second spaced apart magnet pole pieces and are configured to detect gamma rays generated by positron electron annihilation events in a positron emission tomography examination region that at least partially overlaps the magnetic resonance examination region.

In accordance with another aspect, a data acquisition method is disclosed. Magnetic resonance data are acquired using the open magnetic resonance scanner of the combined MR and PET data acquisition system of the preceding paragraph. Simultaneously with the acquiring of magnetic resonance data, PET data are acquired using the first and second arrays of radiation detectors of the combined MR and PET data acquisition system of the preceding paragraph.

In accordance with another aspect, a data acquisition method is disclosed. A static magnetic field is generated at least within a magnetic resonance (MR) examination region. MR data are acquired from the MR examination region. Positron emission tomography (PET) data are acquired from a PET examination region at least partially overlapping the MR examination region. The acquiring of PET data includes amplifying radiation detection event signals by electron multiplication processes configured such that cross products of velocities of accelerating electrons of the electron multiplication processes and the static magnetic field are substantially nulled.

In accordance with another aspect, a positron emission tomography (PET) data acquisition system is disclosed. An array of scintillators surround an examination region and are configured to generate scintillation events responsive to interaction with gamma rays. A plurality of microchannel photomultipliers are optically coupled with the scintillators to detect the scintillation events. A processor is configured to reconstruct projection data or spatially localized projection data derived from the detected scintillation events into a reconstructed positron emission tomographic image.

In accordance with another aspect, a combined magnetic resonance (MR) and positron emission tomography (PET) data acquisition system is disclosed, including: an open magnetic resonance scanner including first and second spaced apart magnet pole pieces, the open magnetic resonance scanner configured to acquire a magnetic resonance image of a subject; a discontinuous array of radiation detectors incompletely encircling said subject and configured to detect 511 keV gamma rays emanating from said subject; and electronics configured to (i) acquire time of flight localized positron emission tomography projection data using the discontinuous array of radiation detectors and (ii) reconstruct a positron emission tomography image of the subject from the time of flight localized positron emission tomography projection data.

In accordance with another aspect, an imaging method is disclosed, comprising: acquiring time of flight localized positron emission tomographic projection data from a subject using an array of radiation detectors that incompletely encircle the subject; and reconstructing an image of the subject from the acquired time of flight localized positron emission tomographic projection data, wherein information missing due to the incomplete encirclement of the subject by the array of radiation detectors is compensated by additional information provided by the time of flight localization.

In accordance with another aspect, a radio frequency coil is disclosed for use in magnetic resonance imaging, the radio frequency coil comprising: a resonant structure having a resonance frequency consonant with a magnetic resonance frequency; a plurality of scintillators secured with the resonant structure; and optical detectors arranged to detect scintillation events emanating from the scintillators.

One advantage resides in facilitating concurrent PET and MR data acquisition.

Another advantage resides in providing a PET/MR scanner employing photomultiplier tube (PMT)-based radiation detectors.

Another advantage resides in providing an open PET/MR scanner.

Another advantage resides in facilitating integration of PET detectors including photomultiplier tubes into an MR scanner.

Still further advantages of the present invention will be appreciated to those of ordinary skill in the art upon reading and understand the following detailed description.

Figure 1:
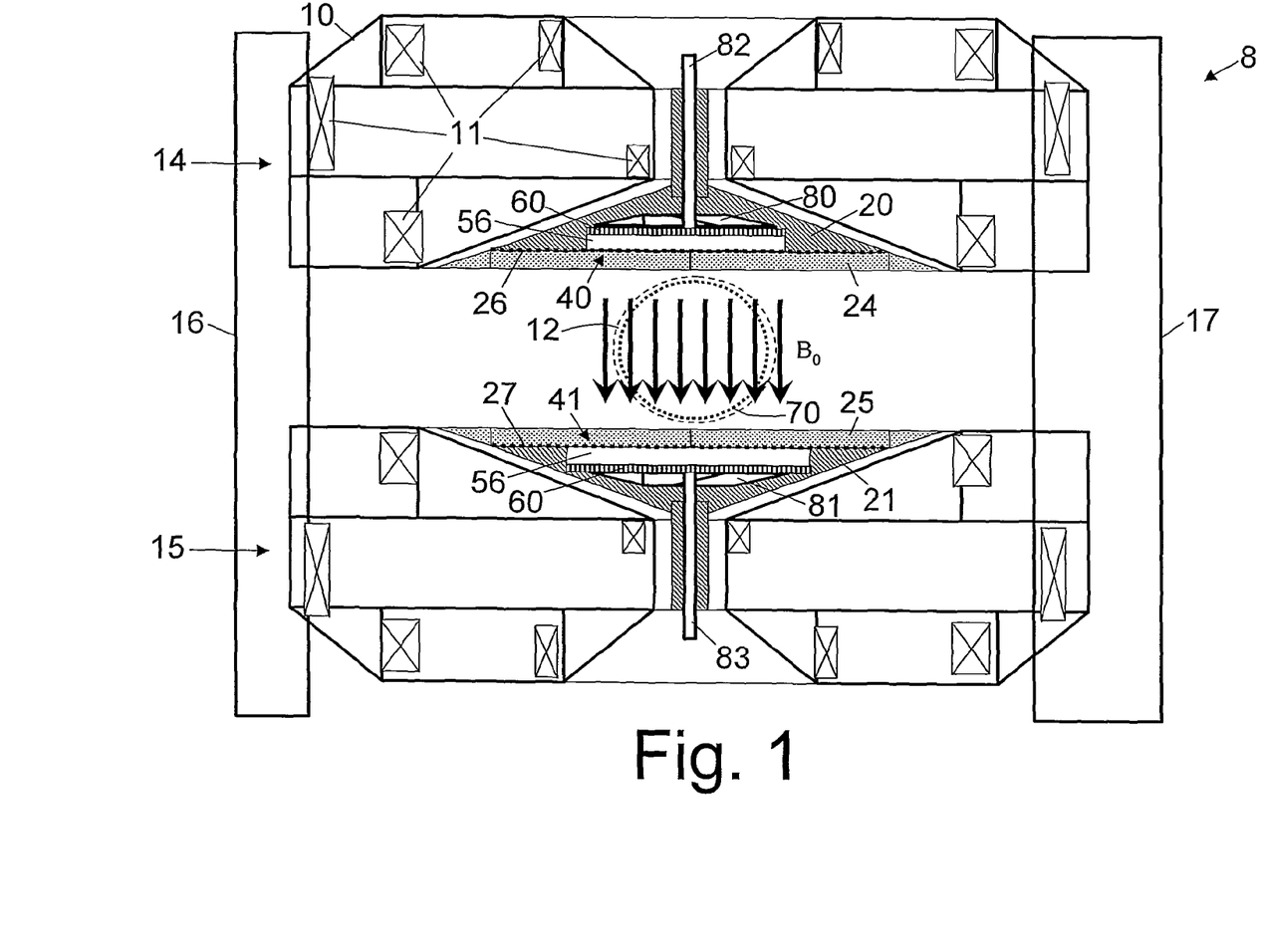
FIG. 1 diagrammatically shows a combined magnetic resonance (MR) and positron emission tomography (PET) data acquisition system including an open MR scanner portion.

With reference to FIG. 1, a combined or hybrid magnetic resonance (MR) and positron emission tomography (PET) data acquisition system 8 is set forth as an illustrative example. A magnetic resonance scanner includes an open magnet 10 including a plurality of conductor coil windings 11 (diagrammatically depicted in FIG. 1 by boxes with crossing lines) that are energized by electrical current to generate a static magnetic field $B_0$ at least within a magnetic resonance examination region 12. The magnetic resonance examination region 12 is indicated by a dashed borderline, and is circular in the illustrated embodiment; however, the magnetic resonance examination region may in general be circular, elliptical, or otherwise-shaped. The conductor coil windings 11 may be superconducting or resistive windings; in the former case the windings are typically disposed in a cryogenic container or other cooling system (not shown). The illustrated magnet 10 is an open magnet having an first and second pole pieces, such as the illustrated upper pole piece 14 and a lower pole piece 15, separated by a gap including the magnetic resonance examination region 12. The illustrated open magnet 10 is a vertical magnet producing the static magnetic field $B_0$ having a vertical (e.g., up or down) magnetic field direction. The illustrated static magnetic field $B_0$ is directed from top-to-bottom, so that the upper pole piece 14 is a north pole while the lower pole piece 15 is a south pole. The opposite polarity is also suitable. In other embodiments, the open magnet may be otherwise oriented to produce a horizontal or otherwise-oriented static magnetic field. In the embodiment illustrated in FIG. 1, at least the upper pole piece 14, and typically also the lower pole piece 15, are supported and spaced apart by vertical frame pieces 16, 17. The frame pieces 16, 17 are illustrative examples; other mechanical support arrangements are conceivable.

The magnetic resonance scanner also includes a magnetic field gradient assembly, which in the illustrative embodiment of FIG. 1 includes upper and lower gradient coil windings 20, 21 that cooperatively superimpose magnetic field gradients on the static $B_0$ magnetic field responsive to selective energizing of selected gradient coil windings. Optionally, the magnetic field gradient coil, magnet, or both may include other features not shown for forming, stabilizing, and dynamically adjusting the magnetic field, such as passive ferromagnetic shims, active shimming coils, or so forth. The magnetic resonance scanner further includes a radio frequency excitation and reception system, such as an illustrated built-in radio frequency coil (indicated diagrammatically) having upper and lower generally planar portions 24, 25 and including a radio frequency screen or shield including upper and lower screen or shield portions 26, 27 (indicated diagrammatically by dashed lines). The radio frequency system includes at least one component, such as the illustrated radio frequency coil 24, 25, that can be energized at a suitable radio frequency to excite magnetic resonance in a subject disposed in the magnetic resonance examination region 12, and typically includes at least one component, such as the illustrated radio frequency coil 24, 25, that can operate as a radio frequency receiver to receive or detect magnetic resonance emanating from the magnetic resonance examination region 12. In some embodiments, different coils are used for the excitation and reception operations. For example, the built-in coil 24, 25 may be used to excite magnetic resonance, and a different, local coil (not shown) may be positioned over or close to the subject in the magnetic resonance examination region 12 to detect magnetic resonance. It is contemplated for the same magnetic resonance scanner to be configurable in different ways using different combinations of built-in coils, local coils, or both.

Figure 2:
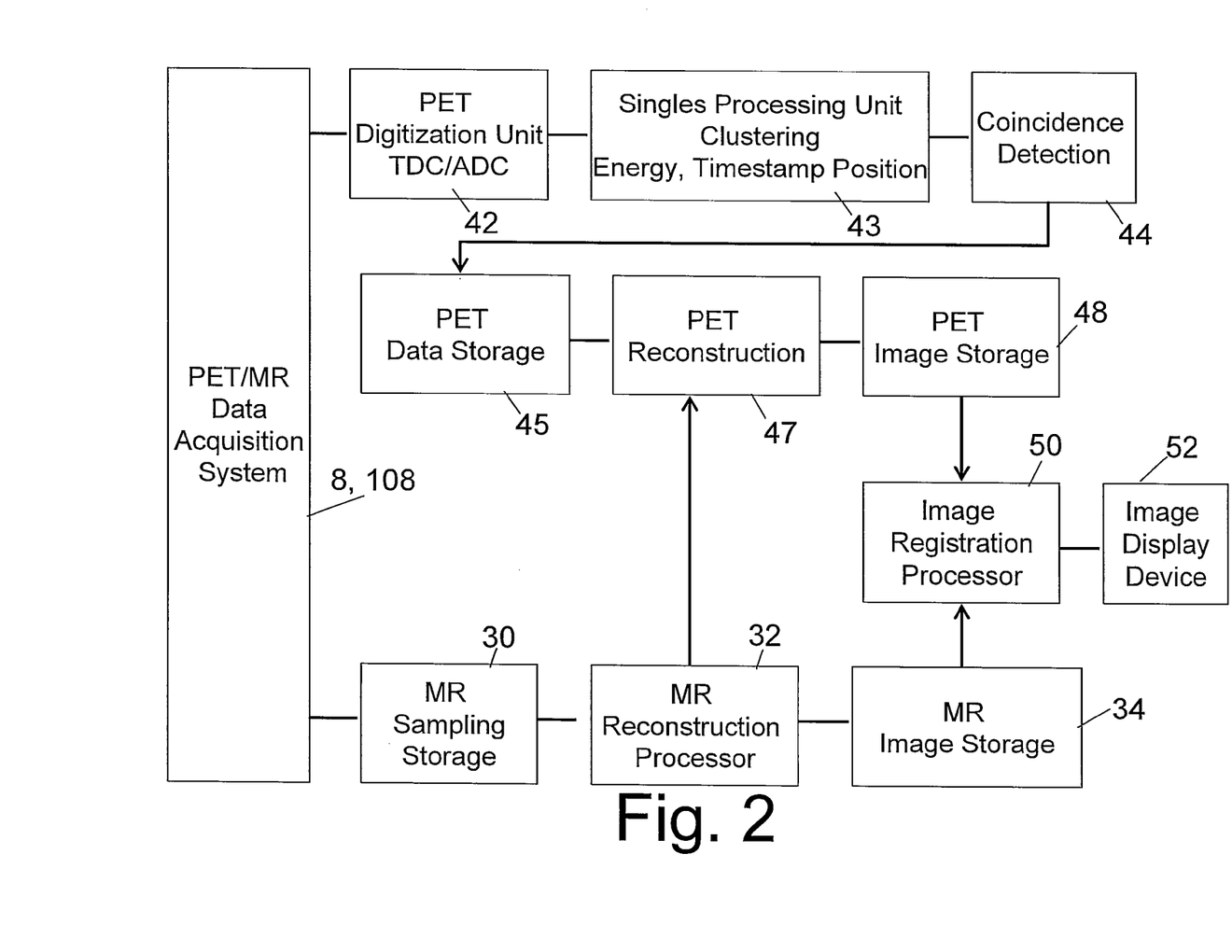
FIG. 2 diagrammatically shows illustrative image processing and display components coupled with the hybrid data acquisition system of FIG. 1.

With continuing reference to FIG. 1 and with brief reference to FIG. 2, in a magnetic resonance imaging session example, the radio frequency excitation system 24, 25 is used to excite magnetic resonance in the subject, while magnetic field gradients applied by the gradient system 20, 21 before, during, or after the magnetic resonance excitation spatially localize the excited magnetic resonance or encode the excited magnetic resonance by frequency-encoding, phase-encoding, or so forth. The excited and spatially encoded magnetic resonance is received using the radio frequency reception system 24, 25 (in this example, the same coil 24, 25 is used for both excitation and reception, but in general different coils may be used) and received magnetic resonance samples are stored in a magnetic resonance sampling storage 30. A magnetic resonance reconstruction processor 32 applies a suitable reconstruction algorithm to reconstruct the magnetic resonance samples to form a reconstructed image that is stored in a magnetic resonance images memory 34. The reconstruction processor 32 applies a reconstruction algorithm that comports with the selected spatial encoding used in generating the magnetic resonance data. For example, a Fourier transform reconstruction algorithm may be suitable for reconstructing Cartesian-encoded magnetic resonance data.

With continuing reference to FIGS. 1 and 2, the combined or hybrid MR and PET data acquisition system 8 further includes radiation detectors for performing PET data acquisition. In the illustrative example of FIG. 1, the radiation detectors include first and second generally planar arrays 40, 41 of radiation detectors. As will be described, each of the illustrated generally planar detector arrays 40, 41 includes a scintillator layer 56 and a layer of electron multiplier-based photon detectors 60; however, other detector configurations are contemplated for use as the arrays 40, 41. The first generally planar array 40 of radiation detectors is arranged between the first magnet pole piece 14 and the first portion 24 of the radio frequency coil. The second generally planar array 41 of radiation detectors is arranged between the second magnet pole piece 15 and the second portion 25 of the radio frequency coil. Each of the generally planar arrays 40, 41 of radiation detectors is configured to detect 511 keV gamma rays that are emitted by positron-electron annihilation events. As is known in the art, when an electron and positron meet, they annihilate, emitting two 511 keV gamma rays that are oppositely directed in accord with the principle of conservation of momentum. (There may be a slight deviation from precise opposition due to carried impulse of the electron and positron prior to annihilation, again in accordance with conservation of momentum). In PET data acquisition, two substantially simultaneous 511 keV gamma ray detection events are presumed to have originated from the same positron-electron annihilation event, which is therefore located somewhere along the "line of response" connecting the two substantially simultaneous 511 keV gamma ray detection events. This line of response is also sometimes called a projection, and the collected PET data is referred to as projection data.

In conventional PET, substantially simultaneous 511 keV gamma ray detection events are defined as two 511 keV gamma ray detection events occurring within a selected short time window, such as within one nanosecond of each other. Due to the variable annihilation position with respect to the detector elements a small (e.g., sub-nanosecond) time difference between the substantially simultaneous gamma photon detection events occurs. A related technique, called time-of-flight PET or TOF-PET, takes advantage of this small time difference to further localize the positron-electron annihilation event along the line-of-response. In general, the annihilation event occurred along the projection at a point closer to the gamma ray detection event that occurred first. If the two gamma ray detection events occur simultaneously within the time resolution of the detectors, then the annihilation event occurred at the midpoint of the projection. The achievable TOF spatial localization along the projection is dependent upon the time resolution, jitter, and other temporal characteristics of the radiation detectors. A projection with TOF spatial localization along the projection is referred to herein as a spatially localized projection.

With continuing reference to FIGS. 1 and 2, the radiation detector arrays 40, 41 of the hybrid system 8 are used to acquire PET or TOF-PET data (that is, projection data or spatially localized projection data). The gamma ray detection events are processed by a PET digitization unit 42 that performs time-to-digital conversion (TDC) and analog-to-digital conversion (ADC) of detection events, and a singles processing unit 43 that performs clustering, energy estimation, timestamping, and positioning. The singles processing unit 43 optionally filters out detections that are outside of a selection energy window centered about on the expected 511 keV gamma ray energy. In some embodiments, the radiation detectors are pixelated, so that the spatial localization of the gamma ray detection events defining the projection correspond to a pixel size (i.e., physical size) of the radiation detectors of the radiation detector arrays 40, 41. In other embodiments, clustering is applied by a block readout algorithm such as Anger logic or the like to provide further spatial localization refinement of the gamma ray detection events defining the projection. A coincidence detection processor 44 employs temporal windowing to identify gamma ray detection events that occurred substantially simultaneously, and hence likely correspond to a common positron-electron annihilation event and hence define a projection or line of response.

For TOF processing, the singles processing 43 and coincidence detection processing 44 can be swapped or interleaved so that the time difference between the identified substantially simultaneous or coincident detection events can be used to spatially localize the positron-electron annihilation event along the projection or line of response. The localization optionally takes the form of a Gaussian or other statistical localization. In one approach, clustered events are input to a three-dimensional position estimation algorithm (for example, implemented using look-up tables) to give local spatial coordinates of the corresponding block detector. Centralized coincidence processing identifies the lines of response. Event information is optionally correlated from coincident radiation detection events to provide refined positioning, and is optionally correlated from neighboring blocks for event synthesis and randoms reduction using knowledge of the Compton scatter cone.

The resulting PET or TOF-PET data are stored in a PET data storage 45. A PET reconstruction processor 47 processes the projection or localized projection data using a suitable reconstruction algorithm to generate a reconstructed image that is stored in a PET images storage 48. For example, a filtered backprojection algorithm or iterative reconstruction algorithm can be employed. The system of FIG. 1 includes an open magnetic resonance scanner and a discontinuous radiation detector array 40, 41 for PET that does not completely encircle the subject. The incomplete encirclement can lead to imaging artifacts due to "missing" projections or lines of response. For example, in the system of FIG. 1 no perfectly horizontal projections are collected, and so information ordinarily provided by such horizontal projections about vertical position is unavailable. Advantageously, if time-of-flight PET data are acquired and reconstructed then the time-of-flight localization provides additional information that compensates for the information that is lost by incomplete encirclement. As a qualitative example, the aforementioned missing information about vertical position can be compensated by a TOF-localized vertical projection, since the temporal localization of the electron-positron annihilation event along the vertical projection provides information about its vertical position.

The MR and PET acquisitions are optionally performed concurrently. As will be discussed, this concurrent acquisition is enabled by configuring the hybrid acquisition system 8 to reduce or eliminate detrimental interaction between the radiation detector arrays 40, 41 of the PET acquisition sub-system and the static magnetic field $B_0$ generated by the magnet 10 of the magnetic resonance acquisition sub-system. Alternatively or additionally, MR and PET acquisition can be done sequentially (e.g., MR first followed by PET, or vice versa) or can be interleaved (e.g., acquire an MR image, a PET image, then translate the patient using a motorized couch or other support to a next imaging position, and repeat the MR and PET acquisitions). An images registration processor 50 optionally spatially registers and optionally temporally registers the reconstructed MR and PET images, and the images as so registered are suitably displayed on an images display device 52, or stored, rendered using suitable two- or three-dimensional rendering software, or otherwise processed.

Figure 3:
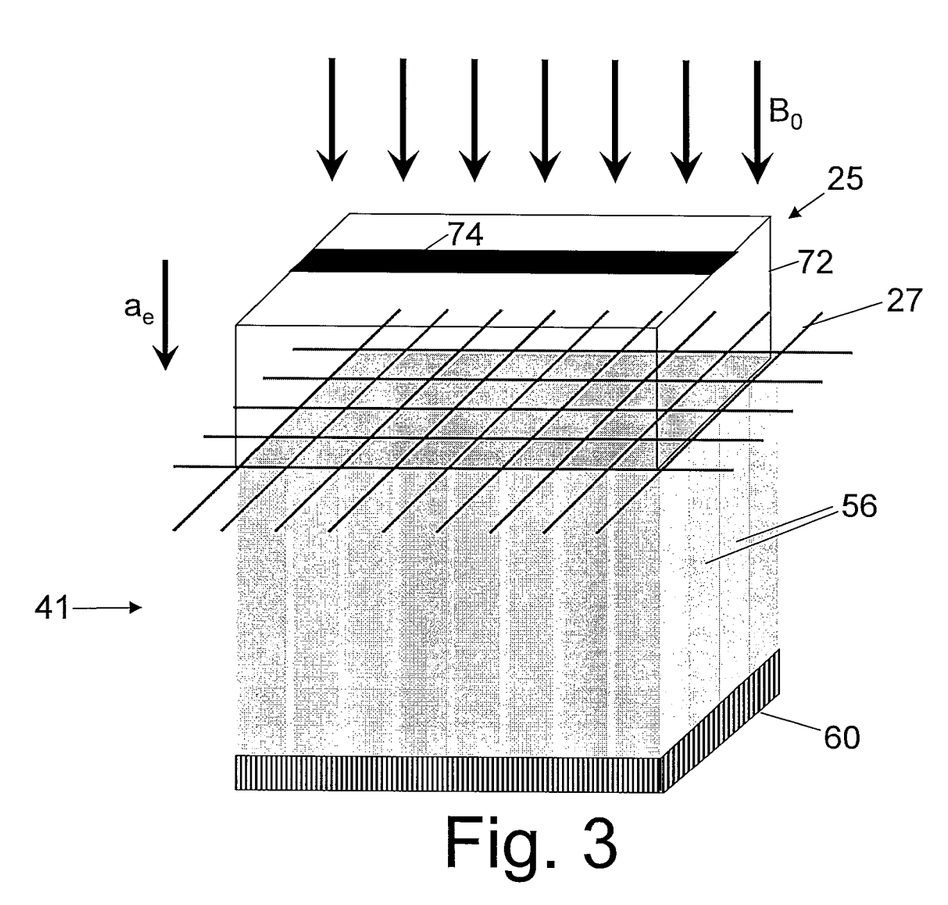
FIG. 3 diagrammatically shows a portion of the lower planar array of radiation detectors of the PET data acquisition portion of the system of FIG. 1.

With reference to FIG. 1 and with further reference to FIG. 3, an embodiment of the radiation detector arrays 40, 41 of the PET acquisition sub-system is described. FIG. 3 depicts a small portion of the lower (or second) radiation detector array 41. The first and second generally planar arrays 40, 41 of radiation detectors are symmetrical in the illustrated embodiment, and each contain a planar array of scintillators 56 and a planar array of electron multiplier elements 60. For time-of-flight PET data acquisition, the scintillators 56 are suitably crystals of $LaBr_3$, LYSO, LGSO, $CeBr_3$, LuI, LSO, or so forth. The scintillators 56 are advantageously selected to be relatively transparent to the magnetic resonance acquisition, and should provide fast scintillation decay times for time-of-flight measurements. Other scintillator materials can also be used. The electron multiplier elements 60 are optically coupled with the scintillators 56 and produce an amplified electrical signal responsive to a burst of light in the optically coupled scintillator through an electron multiplication process. Although not shown, in some embodiments a planar light guide is disposed between the scintillators 56 and the electron multipliers 60. Although the shield 27 is illustrated at the top of the scintillators, it is to be appreciated that it can be positioned at the bottom end or in between the top and bottom.

Figure 4:
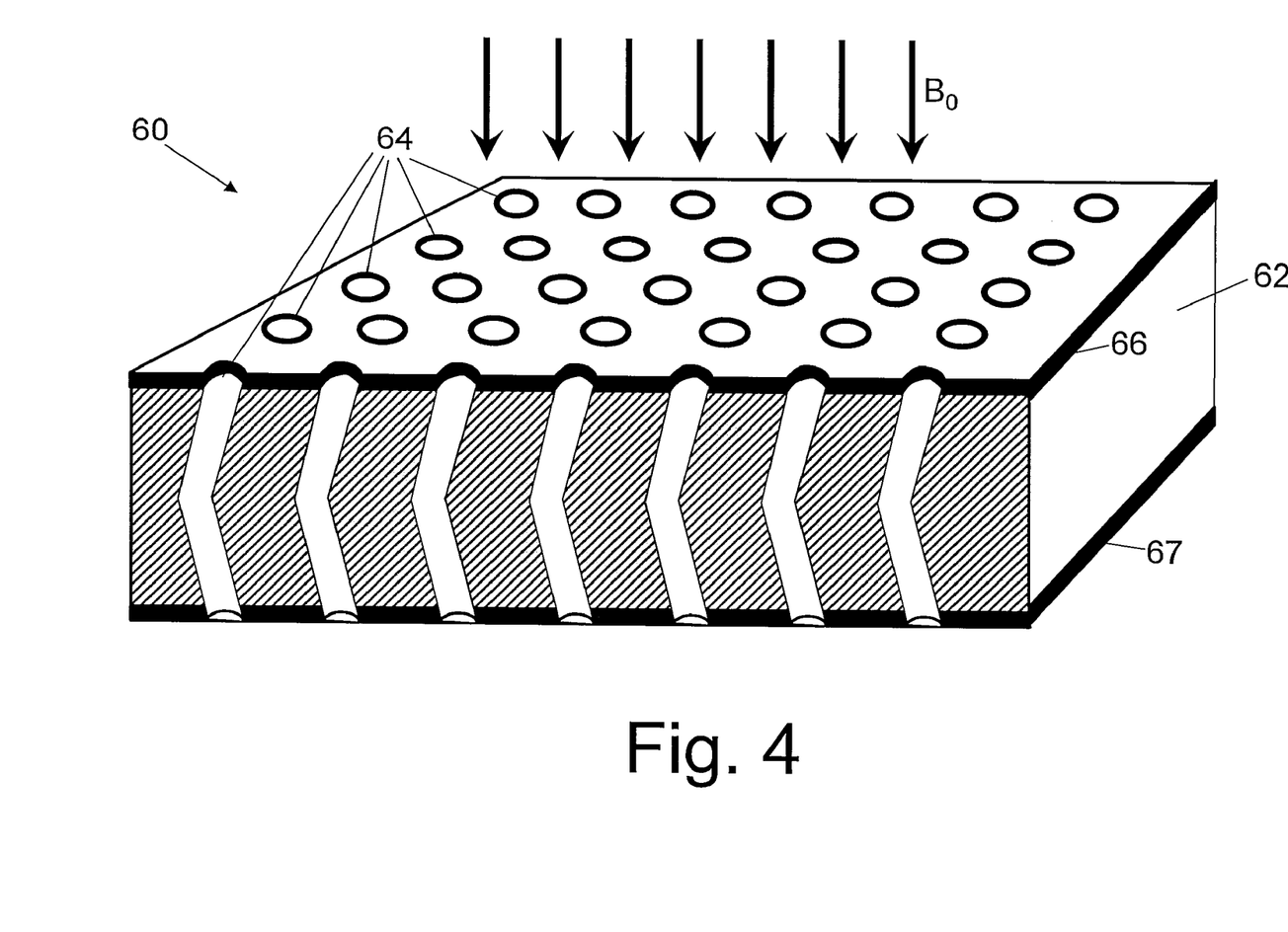
FIG. 4 diagrammatically shows an embodiment of the electron multiplier elements of the lower planar array of radiation detectors of FIG. 4, in which the electron multiplier elements include microchannel plate photomultipliers.

With continuing reference to FIG. 3 and with further reference to FIG. 4, in the illustrated embodiment the electron multiplier elements 60 include microchannel plate photomultipliers. Commercially available microchannel plate photomultipliers are sometimes referred to as "microchannel plate photomultiplier tubes" or "MCP-PMT's". As best seen in FIG. 4, these devices have a microchannel plate 62 of a material having high photoelectric and secondary election emission characteristics. A plurality of parallel microchannels 64 are formed into the microchannel plate 62. The microchannels 64 are pores, tubes, or other parallel narrow openings. Electrodes 66, 67 generate an electrical bias across the length of the microchannels 64. An electron generated near the open end of a microchannel, for example by photoelectric effect responsive to impingement of a photon on a photocathode (not shown), is driven down the microchannel 64 due to the electrical bias on the electrodes 66, 67. As it travels through the microchannel 64, the electron occasionally collides with sides of the microchannel 64. Secondary electron emissions are produced by such collisions, thus providing electron multiplication. At the bottom of the microchannel, the multiplied electrons form an amplified electron signal that is collected by an anode (not shown). Typically, the electron multiplier element 60 together with a suitable photocathode and anode are housed in a vacuum-tight housing. In some embodiments, the material of the electron multiplier 60 may provide the material for the photoelectric effect to generate the initial electrons. In some embodiments the microchannels may be tilted, zigzagged (as shown in FIG. 4), curved, or otherwise-configured to enhance the frequency of electron-microchannel wall collisions. It is also contemplated to use other biasing arrangements than the illustrated arrangement.

Microchannel plate photomultipliers are typically used in photography, night vision goggles, or other applications in which the natural two-dimensional configuration of the microchannels readily provides an addressable two-dimensional optical detector array with built-in amplification. The radiation detector arrays 40, 41 make use of a different advantage of the microchannel plate arrangement. The microchannel plates 62 of the microchannel plate photomultipliers 60 are arranged with the microchannels 64 parallel with the static magnetic field $B_0$. In this configuration the microchannels 64 are arranged to effectively view the scintillators 56 directly and, additionally, a direction of electron acceleration a, along the axes of the microchannels 64 is arranged parallel or anti-parallel with the static magnetic field $B_0$. With this geometry, the cross products of the velocities of accelerating electrons of the electron multiplication processes in the microchannels 62 and the static magnetic field $B_0$ are substantially zero. As a result, the effect of the static magnetic field $B_0$ on the microchannel plate photomultipliers 60 is substantially reduced or eliminated, even though the microchannel plate photomultipliers 60 are disposed within the strong static magnetic field $B_0$.

Figure 5:
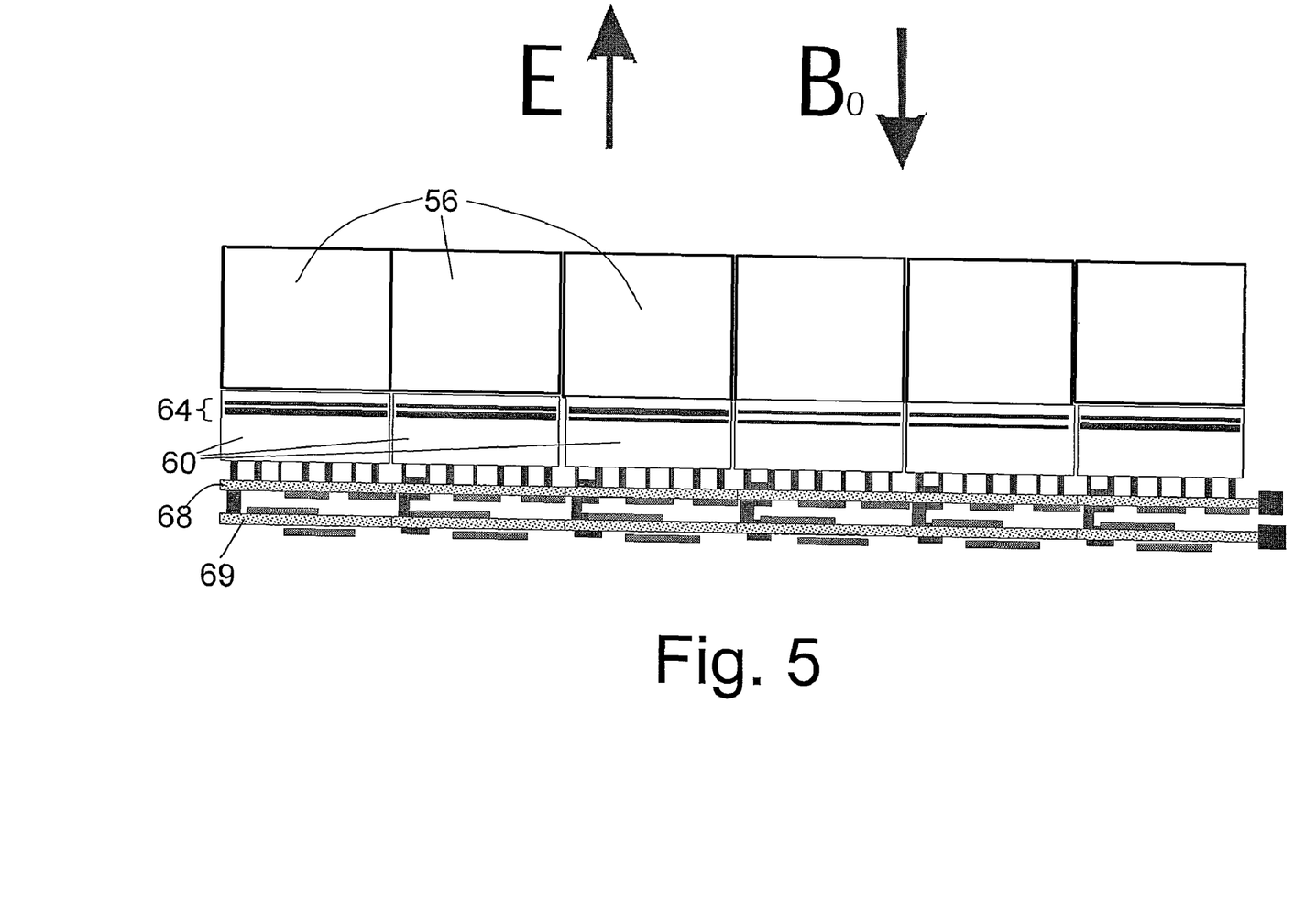
FIG. 5 diagrammatically shows a side view of a planar array of radiation detectors employing a block readout configuration.

With reference to FIG. 5, in some embodiments a block readout configuration is used, in which each scintillator 56 is a block that is viewed by a microchannel plate photomultiplier or an array of SiPMs. In FIG. 5, microchannel plate photomultipliers 60 are used, with the microchannels 64 diagrammatically indicated. By applying a suitable block readout algorithm as part of the singles processing 43, substantial spatial resolution is achievable. For example, with avalanche photo diodes (APDs), a spatial resolution of about 2 mm has been shown to be achievable within a 20×10×10 $mm^3$ LSO scintillator block using block readout processing. See Maas et al., Experimental Characterization of Monolithic-Crystal Small Animal PET Detectors Read Out by APD Arrays, IEEE Trans. Nucl. Sci. vol. 53 no. 3, pp. 1071-77 (2006) which is incorporated herein by reference in its entirety. In the illustrative arrangement of FIG. 5, a first printed circuit board 68 supports electronics, such as microprocessors, application-specific integrated circuits (ASIC's), memory chips, or so forth, that embody the event processors 42, 43 of FIG. 1, or some portion thereof. For example, in some embodiments the electronics of the first printed circuit board 68 embody the TDC/ADC units 42, while the singles processing 43 together with the coincidence detection 44 are performed remotely. In the arrangement illustrated in FIG. 5, a second printed circuit board 69 defines a readout backplane supporting suitable electronics and printed circuitry to read and route off-board the signals generated by the electronics of the first printed circuit board 68.

With reference to FIGS. 1 and 3, the upper and lower photodetector arrays 40, 41 are arranged to view a positron emission tomography (PET) examination region 70 through respective upper and lower generally planar portions 24, 25 of the radio frequency coil. The PET examination region 70 is indicated by a dotted borderline, and is circular in the illustrated embodiment; however, the PET examination region may in general be circular, elliptical, or otherwise-shaped. In the illustrative example of FIG. 3, the radio frequency coil includes a printed circuit board 72 having printed conductors, such as the illustrated printed conductor portion 74, formed on a front surface. The radio frequency shield or screen 27 can be a free-standing wire mesh, or a conductor mesh printed or otherwise disposed on a printed circuit board 72 or other substrate, or so forth. The upper planar portion 24 of the radio frequency coil suitably has the same configuration. In the arrangement shown, the radio frequency coil 24, 25 should be substantially transparent to 511 keV gamma rays, so that the radio frequency coil 24, 25 does not block the view of the PET examination region 70 by the photodetector arrays 40, 41. In the illustrated embodiment, the PET examination region 70 is slightly smaller than the MR examination region 12. In other embodiments, the MR examination region may be the smaller region, or the centroid of the MR examination and the centroid of the PET examination region may be relatively offset from one another, or so forth. If there is at least some overlap of the MR and PET examination regions, then acquisition of both MR and PET imaging data of the same portion of the subject is possible without moving the subject between the MR and PET acquisitions. Indeed, it is contemplated to acquire PET and MR imaging data from the same region of the subject simultaneously, or in an interleaved fashion.

With reference to FIG. 1, the photodetector arrays 40, 41 further include respective suitable circuitry 80, 81 for reading the electron multiplier elements 60. For example, the circuitry 80, 81 may include the PET digitization processing 42 and optionally the singles processing 43 for digitizing the energy of the amplified signals indicative of gamma ray detection events. The event information can either be self-triggered or common triggered by using a locally installed neighbor logic or analog circuitry. The processing units collecting this data optionally perform offset, gain, time-walk, or other corrections, as well as optional sorting and optional event clustering. In the illustrated open MR scanner configuration, passthroughs in the magnet 10 provide conduits 82, 83 for conveying electrical power, optional detector cooling, signal transmission, or so forth. In some embodiments, some of the circuitry 80, 81 may be located remote from the electron multiplier elements 60.

An advantage of the configuration shown in FIGS. 1 and 3 is compactness—the planar photodetector arrays 40, 41 do not take up a lot of space in the gap between the north and south magnet poles 14, 15.

Figure 6:
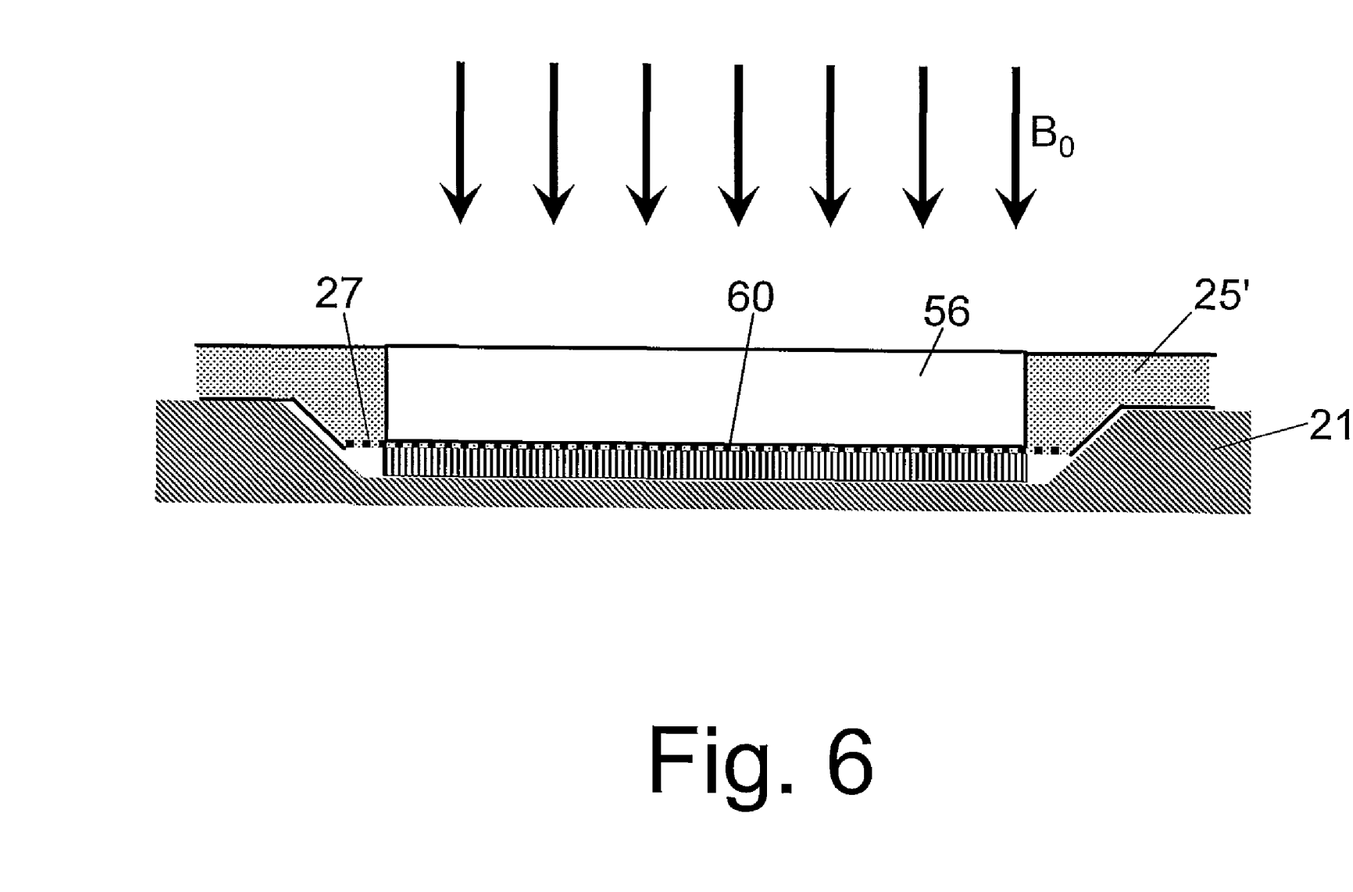
FIGS. 6 and 7 show portions of alternative embodiments of the lower planar array of radiation detectors of the PET data acquisition portion of the system of FIG. 1, in which the scintillators are wholly (FIG. 6) or partially (FIG. 7) spatially integrated with the radio frequency coil.

With reference to FIG. 6, a modified embodiment is illustrated in which the planar photodetector arrays 40, 41 take up still less space in the gap between the north and south magnet poles 14, 15. In this embodiment, the scintillators 56 are integrated into a modified radio frequency coil 25'. For example, the scintillators 56 may be incorporated into the printed circuit board 72 that supports the conductors 74 of the radio frequency coil. In some embodiments, the scintillators 56 are formed as pixels sized to align with gaps of a conductive mesh optionally forming the radio frequency shield or screen 27. In some embodiments, the wire mesh incorporates resonant circuits that provide a high impedance for gradient fields produced by the gradient coils 21, and low impedance for the radio frequency field generated by the radio frequency coil. For a static magnetic field $B_0$ greater than or about 1.5 Tesla, the diameter of wires of a conductive mesh forming the radio frequency shield or screen can be less than 0.1 millimeters. If a planar light guide (not shown) is inserted between the scintillators 56 and the electron multiplier elements 60, then the light guide can be used as a substrate for supporting the wire mesh and the wire mesh can define alignment features for positioning blocks of the scintillators 56.

Figure 7:
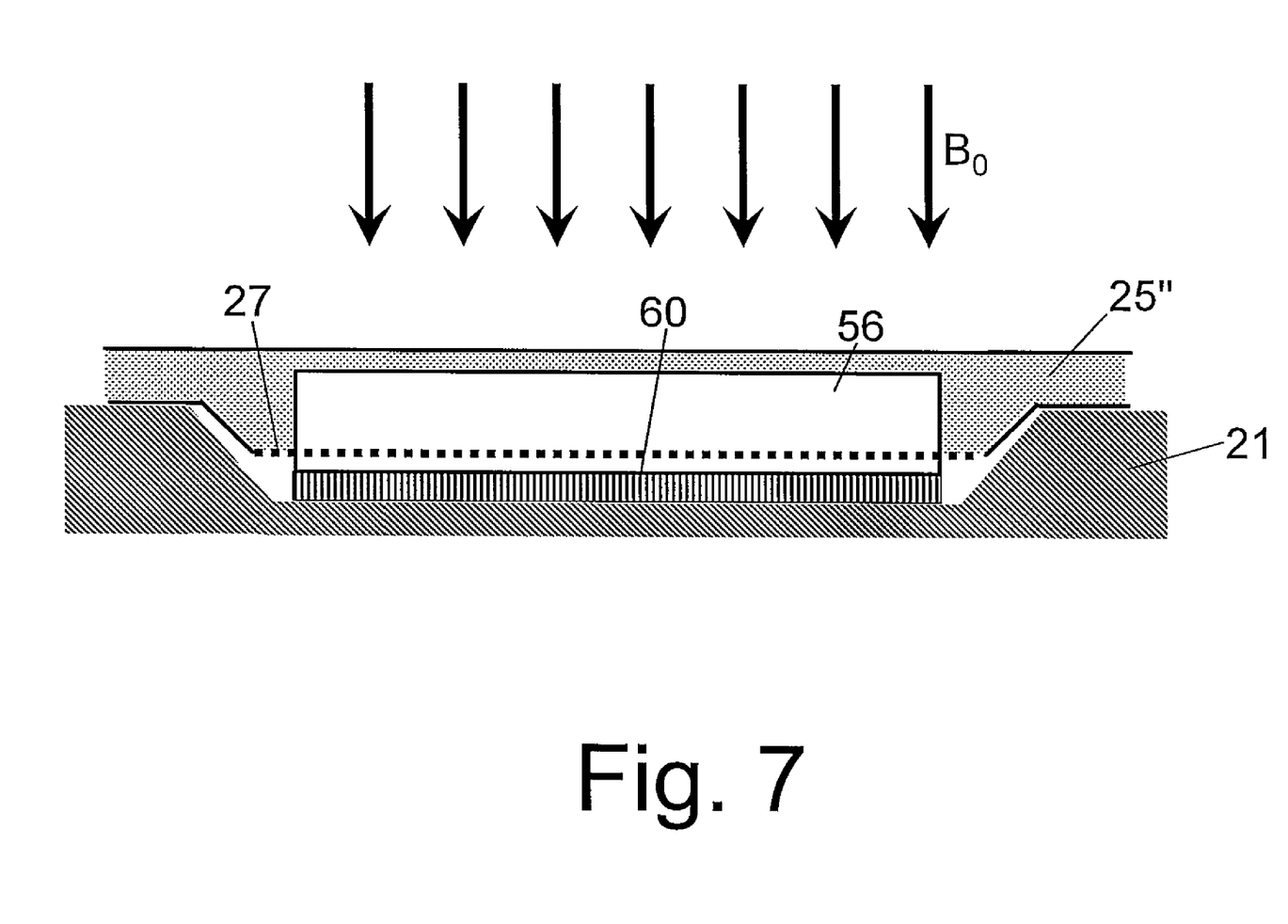

With reference to FIG. 7, an intermediate embodiment is illustrated in which the planar photodetector arrays 40, 41 take up an intermediate amount of space in the gap between the north and south magnet poles 14, 15. In this embodiment, the scintillators 56 are partially integrated into a modified radio frequency coil 25". For example, the scintillators 56 may be protrude into a recess of the printed circuit board 72 that supports the conductors 74 of the radio frequency coil.

Figure 8:
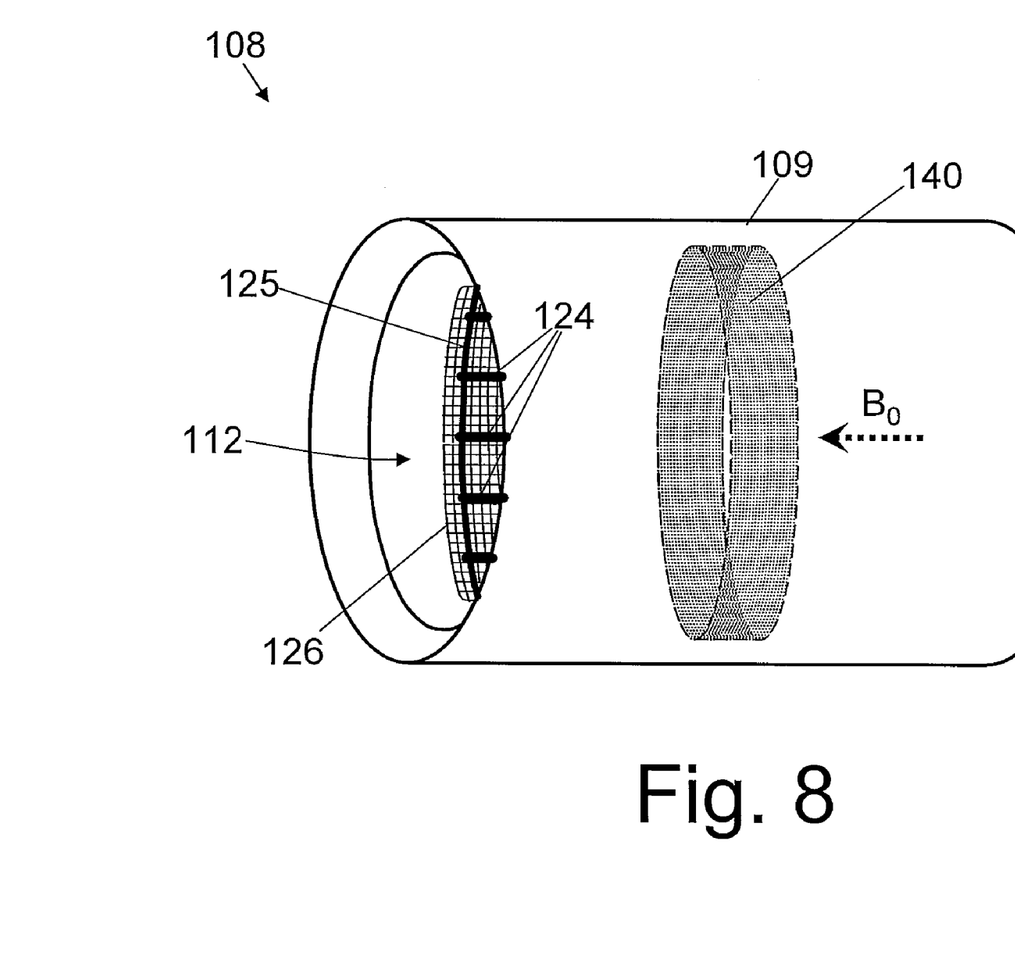
FIGS. 8 and 9 diagrammatically show perspective and end sectional views, respectively, of a combined magnetic resonance (MR) and positron emission tomography (PET) data acquisition system including a closed bore-type MR scanner portion.
Figure 9:
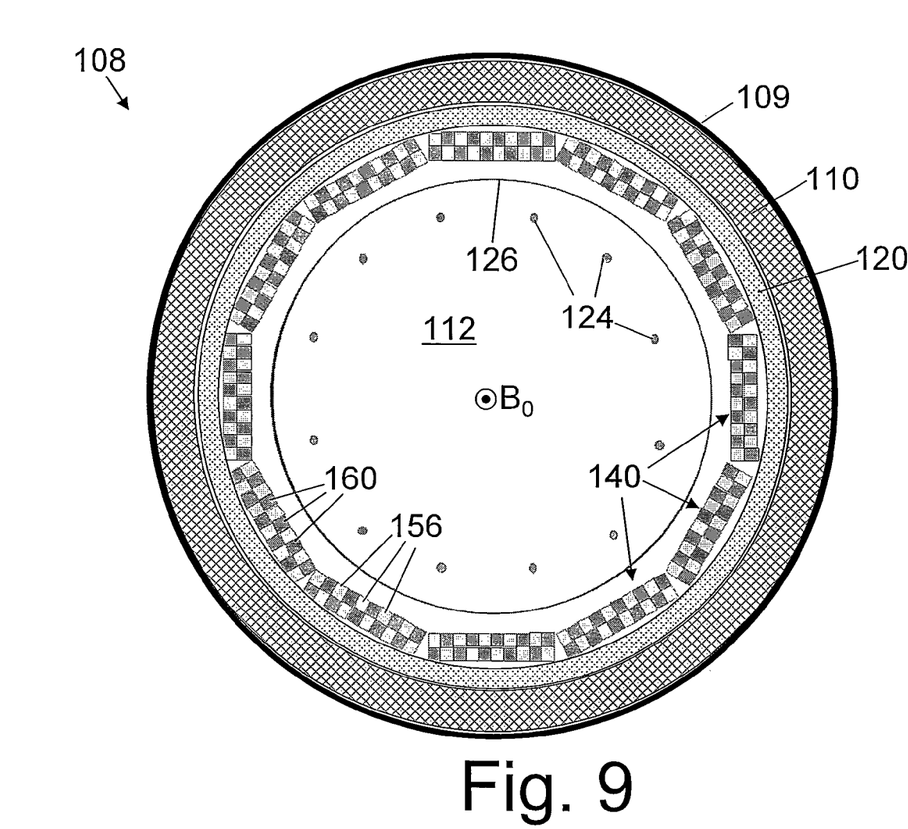

With reference to FIGS. 8 and 9, a hybrid or combined magnetic resonance (MR) and positron emission tomography (PET) data acquisition system 108 is shown. A magnetic resonance scanner includes a closed bore-type scanner housing 109 that contains a solenoidal-type magnet 110 having a plurality of conductor coil windings arranged to generate a static magnetic field $B_0$ within and parallel with the axis of a generally cylindrical bore opening 112 defined by the housing. The magnet may be a superconducting or resistive magnet; in the former case the magnet is typically disposed in a cryogenic container or other cooling system within the bore-type scanner housing 110. The scanner housing 110 also contains a magnetic field gradient assembly 120, such as magnetic field gradient coils that cooperatively superimpose magnetic field gradients on the static $B_0$ magnetic field responsive to selective energizing of selected gradient coil windings. Optionally, the magnetic field gradient coil, magnet, or both may include other features not shown for forming, stabilizing, and dynamically adjusting the magnetic field, such as passive ferromagnetic shims, active shimming coils, or so forth.

The magnetic resonance scanner further includes a radio frequency excitation and reception system, such as an illustrated built-in birdcage or transverse electromagnetic (TEM)-type "whole-body" radio frequency coil having rungs or rods 124 and a radio frequency screen or shield 126. In a birdcage-type coil, the rungs 124 are connected by end-rings 125 (one end-ring 125 is depicted as an example in FIG. 8; no end-rings are shown in FIG. 9) to generate and optionally detect magnetic resonance over a substantial region of the bore opening 112. In a TEM-type whole-body coil, the end-rings 125 are omitted, and the rods 124 are connected at their ends to the radio frequency shield or screen 126 to generate and optionally detect magnetic resonance of a substantial region of the bore opening 112. In either a birdcage or TEM-type coil, the radio frequency shield or screen 126 is typically a thin cylindrical conductive mesh or a resonant screen. In other embodiments, one or more local radio frequency coils (not shown) used exclusively or in conjunction with the whole-body coil 124, 126 for magnetic resonance excitation and/or detection.

With continuing reference to FIGS. 8 and 9, the combined or hybrid MR and PET data acquisition system 108 further includes radiation detectors 140 for performing PET data acquisition. In the illustrative example of FIGS. 8 and 9, these radiation detectors 140 are arranged as a short-axis cylindrical array centered around the isocenter of the MR magnet. In FIG. 8, the radiation detectors 140 are shown in phantom for illustrative purposes, but it is to be understood that the radiation detectors 140 are typically blocked from view by the scanner housing 109. The cylindrical array of radiation detectors 140 surround and are coaxial with the bore opening 112 of the MR scanner. As shown in FIG. 9, in the illustrated embodiment the radiation detectors 140 are at a radius (i) smaller than the radius of the gradient assembly 120 and (ii) larger than the radius of the radio frequency screen or shield 126. That is, the radiation detectors 140 are placed between the gradient assembly 120 and the radio frequency screen or shield 126. Alternatively, the radiation detectors 140 could be arranged inside of (i.e., at a smaller radius than) the shield 126 and outside of (i.e., at a larger radius than) the rungs or rods 124. In other embodiments, the radiation detectors 140 are arranged inside of the shield 126 and inside of the rungs or rods 124. In other embodiments, the radiation detectors 140 are arranged at about the same radius as the rungs or rods 126, for example between the rungs or rods. However they are arranged, the radiation detectors 140 should have a substantially unimpeded view of the examination region within the bore opening 112 respective to 511 keV gamma rays; intervening components should be either narrow (e.g., the rungs or rods 124) or substantially transparent to 511 keV gamma rays (e.g., the radio frequency screen or shield 126).

Figure 10:
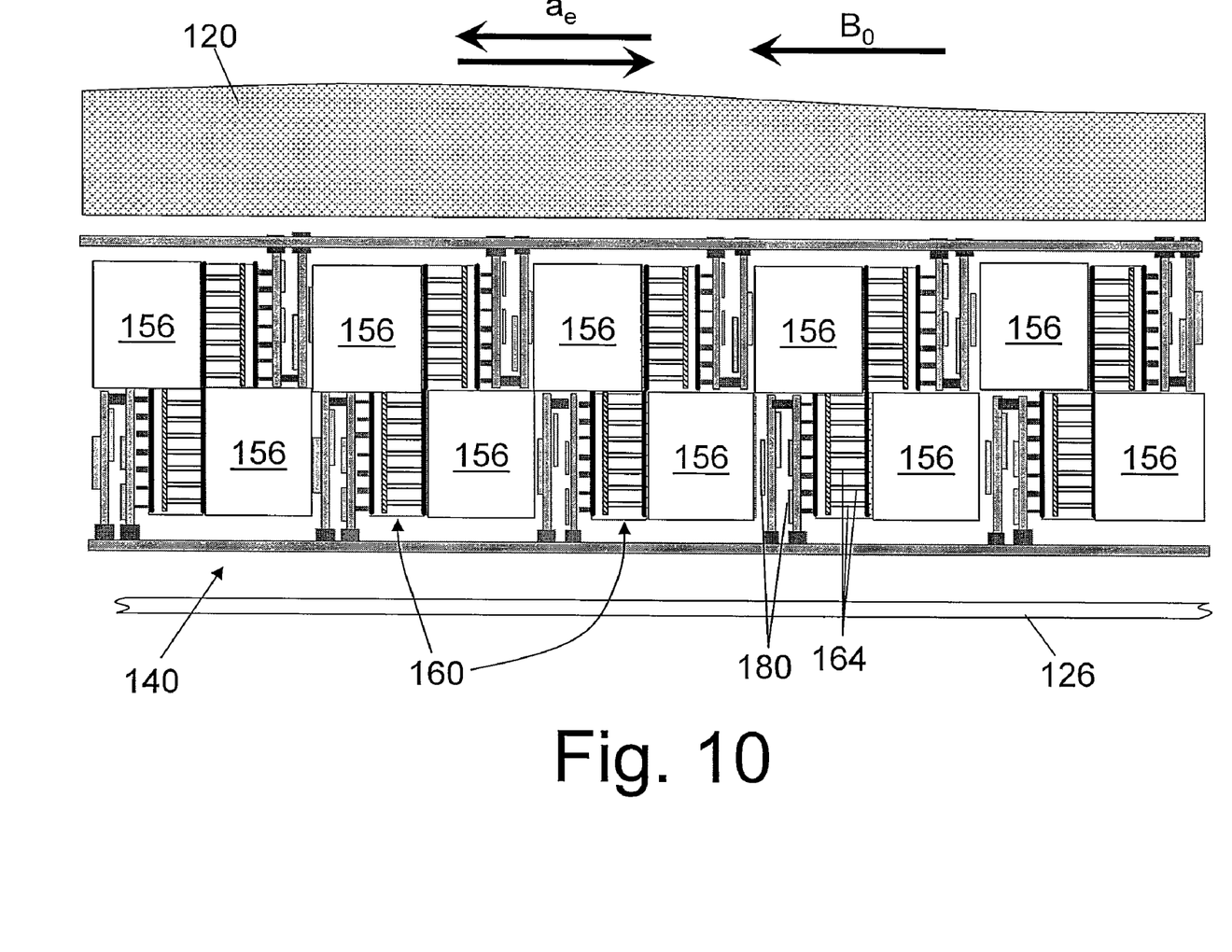
FIG. 10 diagrammatically shows a portion of the array of radiation detectors of the PET data acquisition portion of the system of FIGS. 8 and 9 viewed from the bore outward.

With continuing reference to FIGS. 8 and 9 and with further reference to FIG. 10, an embodiment of the radiation detectors 140 of the PET acquisition sub-system is described. FIG. 10 depicts a small portion of the array of radiation detectors 140 including ten scintillator blocks 156 and corresponding electron multiplier elements 160. The illustrated electron multiplier elements 160 include microchannel plate photomultipliers, such as commercially available microchannel plate photomultipliers sometimes referred to as "microchannel plate photomultiplier tubes" or "MCP-PMT's". The electron multiplier elements 160 are suitably similar to the electron multipliers 60 depicted in FIG. 4, and include microchannels 164. As in the case of the acquisition system 8, the microchannel plate photomultipliers 160 of the acquisition system 108 are preferably arranged with their direction of electron acceleration $a_e$ parallel or anti-parallel with the static magnetic field $B_0$. For the configuration of radiation detectors 140 illustrated in FIG. 10, the top layer the direction of electron acceleration $a_e$ is anti-parallel with the direction of the static magnetic field $B_0$, while for the bottom layer the direction of electron acceleration $a_e$ is parallel with the direction of the static magnetic field $B_0$. In FIG. 10, the microchannels 164 are diagrammatically indicated and are arranged parallel with the static magnetic field $B_0$ so that the electric field generated by the biasing of the electrodes of the microchannel plate photomultipliers 160 along the length of the microchannels 164 produces the electron acceleration $a_e$ oriented parallel or anti-parallel with the static magnetic field $B_0$. The resulting geometric arrangement has the microchannel plate photomultipliers 160 arranged at the sides of their respective scintillators 156. This side-by-side arrangement results in gaps between the scintillators 156 to accommodate these microchannel plate photomultipliers 160 and associated electronics or circuitry. To address these gaps, the radiation detectors 140 shown in FIG. 10 are arranged in a double layer with the scintillators 156 in the second layer offset from those of the first layer to fill in the gaps. This approach is suitable if the microchannel plate photomultipliers 160 are substantially transparent to 511 keV gamma rays. More generally, the scintillators 156 and microchannel plate photomultipliers 160 are optionally interleaved in one or more detector layers, with each detector layer having a surface normal oriented transverse to the direction of the static magnetic field $B_0$. For a cylindrical magnet, the one or more interleaved detector layers each define a generally cylindrical shell arranged coaxially with the generally cylindrical magnet 110. If the microchannel plate photomultipliers are not sufficiently transparent, then a single layer can be used, albeit with some loss of resolution.

In the illustrated embodiment, each scintillator 156 is a block that is viewed from the side by an 8×8 array of microchannel plate photomultipliers 160, and Anger logic or another suitable block readout algorithm is used to enhance spatial resolution based on the relative signals received by the elements of the 8×8 array of microchannel plate photomultipliers 160. In other embodiments, pixelated scintillators may be used, or block scintillators may be used with viewing microchannel plate photomultiplier arrays of other sizes. Suitable circuitry 180 for reading the electron multiplier elements 160 is integrated into the radiation detectors 140 as application-specific integrated circuitry (ASIC) or microprocessor components. For example, the circuitry 180 may include analog-to-digital converters (ADC) for digitizing the energy of the amplified signals indicative of gamma ray detection events, time-to-digital converters (TDC) for generating digital timestamps for gamma ray detection events, and so forth. The event information can either be self-triggered or common triggered by using a locally installed neighbor logic or analog circuitry. The processing units collecting this data optionally perform offset, gain, time-walk, or other corrections, as well as optional sorting and optional event clustering. Optionally, the circuitry 180 includes portions or all of the PET events processing 42, 43.

Like the acquisition system 8, the acquisition system 108 is optionally configured for simultaneous MR and PET imaging if the MR and PET examination regions at least partially overlap. Additionally or alternatively, MR and PET imaging may be performed in succession or may be interleaved, for example on a slice-by-slice basis.

The illustrated embodiments employ electron multiplier elements 56, 156 that are advantageously arranged with the direction of electron acceleration $a_e$ substantially parallel or anti-parallel with a magnetic field direction of the static magnetic field $B_0$ generated by the magnetic resonance scanner. In other contemplated embodiments, detectors that are relatively insensitive to magnetic field are substituted for the electron multiplier elements. Such detectors may include, for example, avalanche photodiodes (APD's) or solid state silicon photomultipliers (SiPM). Some suitable SiPM detectors are described in International Publication WO 2006/111869, and in International Publication WO 2006/111883. Optionally, the radiation detectors 40, 41, 140 (or selected units or portions thereof) are surrounded radio frequency-tight and light-tight shielding (not shown) to protect the detectors and electronics. Mu-metal shielding (not shown) is optionally included as well. The illustrated open and bore-type magnetic resonance scanners are illustrative examples, and other types of MR scanners are contemplated.

Having thus described the preferred embodiments, the invention is now claimed to be:

1. A combined magnetic resonance (MR) and positron emission tomography (PET) data acquisition system comprising:
    a magnetic resonance scanner including a magnet configured to generate a static magnetic field at least in a magnetic resonance examination region, the magnetic resonance scanner being configured to acquire magnetic resonance data from the magnetic resonance examination region; and
    radiation detectors configured to detect gamma rays generated by positron-electron annihilation events in a positron emission tomography examination region, the radiation detectors including electron multiplier elements having a direction of electron acceleration arranged substantially parallel or anti-parallel with the static magnetic field.

2. The acquisition system as set forth in claim 1, wherein the positron emission tomography examination region and the magnetic resonance examination region at least partially overlap.

3. The acquisition system as set forth in claim 2, wherein the radiation detectors include:
    first and second parallel planar arrays of radiation detectors arranged to view the positron emission tomography examination region, the first and second parallel planar arrays arranged orthogonal to the static magnetic field.

4. The acquisition system as set forth in claim 2, wherein the magnetic resonance scanner further includes:
    a radio frequency coil including a radio frequency screen or shield, the radio frequency coil having first and second planar portions arranged parallel with the respective first and second parallel planar arrays of radiation detectors.

5. The acquisition system as set forth in claim 1, wherein the magnetic resonance scanner includes a generally cylindrical magnet generating the static magnetic field oriented parallel with a cylinder axis of the generally cylindrical magnet, and the radiation detectors are arranged inside of the generally cylindrical magnet.

6. The acquisition system as set forth in claim 1, wherein the radiation detectors further include scintillators each being optically coupled with a plurality of the electron multiplier elements, the data acquisition system further including:
    a processor configured to compute a localized position of a burst of light generated within one of the scintillators based on detected signals from the plurality of electron multiplier elements optically coupled therewith.

7. The acquisition system as set forth in claim 6, further including:
    a radio frequency shield disposed between the electron multiplier elements and the examination region.

8. A data acquisition method comprising:
    (i) acquiring magnetic resonance data using the magnetic resonance scanner of the combined MR and PET data acquisition system of claim 1; and
    (ii) acquiring PET data using the radiation detectors of the combined MR and PET data acquisition system of claim 1;
    wherein the acquiring (i) and the acquiring (ii) are performed simultaneously.

9. A combined magnetic resonance (MR) and positron emission tomography (PET) data acquisition system comprising:
    a magnetic resonance scanner including a magnet configured to generate a static magnetic field at least in a magnetic resonance examination region, the magnetic resonance scanner being configured to acquire magnetic resonance data from the magnetic resonance examination region; and
    first and second parallel planar arrays of radiation detectors arranged to view a positron emission tomography examination region that at least partially overlaps the magnetic resonance examination region, the first and second parallel planar arrays arranged orthogonal to the static magnetic field, the radiation detectors being configured to detect gamma rays generated by positron-electron annihilation events in the positron emission tomography examination region, wherein each planar array of radiation detectors includes:
        a planar array of microchannel plate photomultipliers, electron-transmissive microchannels of the microchannel plate photomultipliers being arranged parallel with the static magnetic field, and
        a planar array of scintillators arranged parallel with the planar array of microchannel plate photomultipliers and disposed between the planar array of microchannel plate photomultipliers and the positron emission tomography examination region.

10. A combined magnetic resonance (MR) and positron emission tomography (PET) data acquisition system comprising:
    a magnetic resonance scanner including a generally cylindrical magnet configured to generate a static magnetic field at least in a magnetic resonance examination region that is oriented parallel with a cylinder axis of the generally cylindrical magnet, the magnetic resonance scanner being configured to acquire magnetic resonance data from the magnetic resonance examination region; and
    radiation detectors arranged inside of the generally cylindrical magnet and configured to detect gamma rays generated by positron-electron annihilation events in a positron emission tomography examination region, the radiation detectors including electron multiplier elements having a direction of electron acceleration arranged substantially parallel or anti-parallel with the static magnetic field, wherein the radiation detectors include:
  scintillators arranged inside of the generally cylindrical magnet; and
  microchannel plate photomultipliers arranged to view the scintillators, electron-transmissive microchannels of the microchannel plate photomultipliers being arranged parallel with the static magnetic field and parallel with the cylinder axis of the generally cylindrical magnet.

11. A combined magnetic resonance (MR) and positron emission tomography (PET) data acquisition system comprising:
  a magnetic resonance scanner including a magnet configured to generate a static magnetic field at least in a magnetic resonance examination region, the magnetic resonance scanner being configured to acquire magnetic resonance data from the magnetic resonance examination region; and
  radiation detectors configured to detect gamma rays generated by positron-electron annihilation events in a positron emission tomography examination region, the radiation detectors including electron multiplier elements having a direction of electron acceleration arranged substantially parallel or anti-parallel with the static magnetic field;
  wherein the magnet generates a static magnetic field between a pair of pole pieces, the radiation detectors being mounted adjacent and parallel to at least one of the pole pieces.

12. A combined magnetic resonance (MR) and positron emission tomography (PET) data acquisition system comprising:
  an open magnetic resonance scanner having first and second spaced-apart magnet pole pieces disposed on opposite sides of a magnetic resonance examination region wherein a static magnetic field at least in the magnetic resonance examination region has a magnetic field direction directed from the first magnet pole piece to the second magnet pole piece; and
  first and second arrays of radiation detectors disposed with the first and second spaced-apart magnet pole pieces and configured to detect gamma rays generated by positron-electron annihilation events in a positron emission tomography examination region that at least partially overlaps the magnetic resonance examination region;
  wherein the radiation detectors of the first and second arrays of radiation detectors include electron multiplier elements disposed with the first and second spaced-apart magnet pole pieces.

13. The data acquisition system as set forth in claim 12, wherein the first and second arrays of radiation detectors are first and second planar arrays oriented parallel to each other and transverse to the static magnetic field.

14. The data acquisition system as set forth in claim 13, wherein the radiation detectors of the first and second arrays of radiation detectors include at least one of microchannel plate photomultipliers, avalanche photodiodes (APD's), and solid state silicon photomultipliers (SiPM).

15. The data acquisition system as set forth in claim 12, wherein the open magnetic resonance scanner includes:
  a radio frequency coil having first and second planar portions arranged parallel with the first and second planar arrays of radiation detectors.

16. The data acquisition system as set forth in claim 12, wherein the radiation detectors of the first and second arrays of radiation detectors include:
  microchannel plate photomultipliers having electron-transmissive microchannels arranged parallel with the static magnetic field; and
  scintillators arranged to generate bursts of light responsive to interaction with gamma rays, the microchannel plate photomultipliers being optically coupled with the scintillators to detect the generated bursts of light.

17. The data acquisition system as set forth in claim 12, further including:
  electronics configured to acquire time-of-flight positron emission tomography data using the first and second arrays of radiation detectors.

* * * * *